US006855145B2

(12) United States Patent
Ciarrocca

(10) Patent No.: US 6,855,145 B2
(45) Date of Patent: Feb. 15, 2005

(54) SELF-WETTING, DRY-FIELD BIPOLAR ELECTRODES FOR ENDOSCOPIC SURGERY

(75) Inventor: Scott Ciarrocca, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 91 days.

(21) Appl. No.: 10/266,386

(22) Filed: Oct. 8, 2002

(65) Prior Publication Data

US 2003/0073993 A1 Apr. 17, 2003

Related U.S. Application Data

(60) Provisional application No. 60/327,933, filed on Oct. 9, 2001.

(51) Int. Cl.[7] ............................................... A61B 18/18
(52) U.S. Cl. ........................................ 606/41; 607/101
(58) Field of Search ................. 606/41–51; 607/96–102

(56) References Cited

U.S. PATENT DOCUMENTS

| 5,542,945 | A | | 8/1996 | Fritzsch |
| 6,355,034 | B2 | | 3/2002 | Cosmescu |
| 6,382,968 | B2 | * | 5/2002 | Livaditis ...................... 433/32 |
| 6,652,518 | B2 | * | 11/2003 | Wellman et al. .............. 606/41 |
| 2002/0058934 | A1 | * | 5/2002 | Wang et al. ................... 606/41 |

OTHER PUBLICATIONS

PCT International Search Report, PCT/US02/32258, May 9, 2003.

* cited by examiner

*Primary Examiner*—Roy D. Gibson

(57) ABSTRACT

An electrosurgical probe and method for using the same is provided. The electrosurgical probe includes a distal end and a proximal end, with the distal end having a configuration defining an outer convex face and an inner concave face. At least one active electrode and at least one return electrode are mounted on the inner concave face.

9 Claims, 5 Drawing Sheets

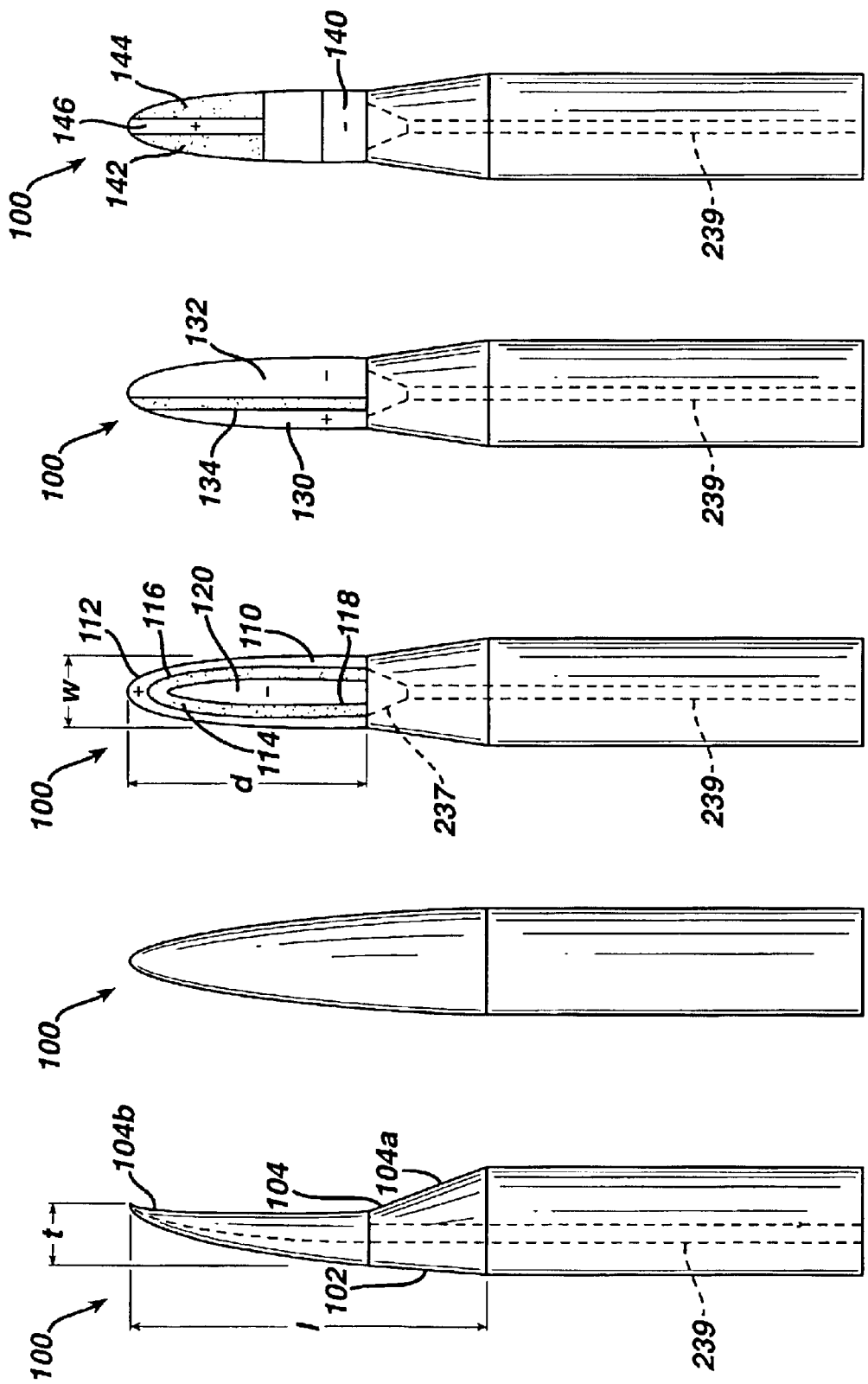

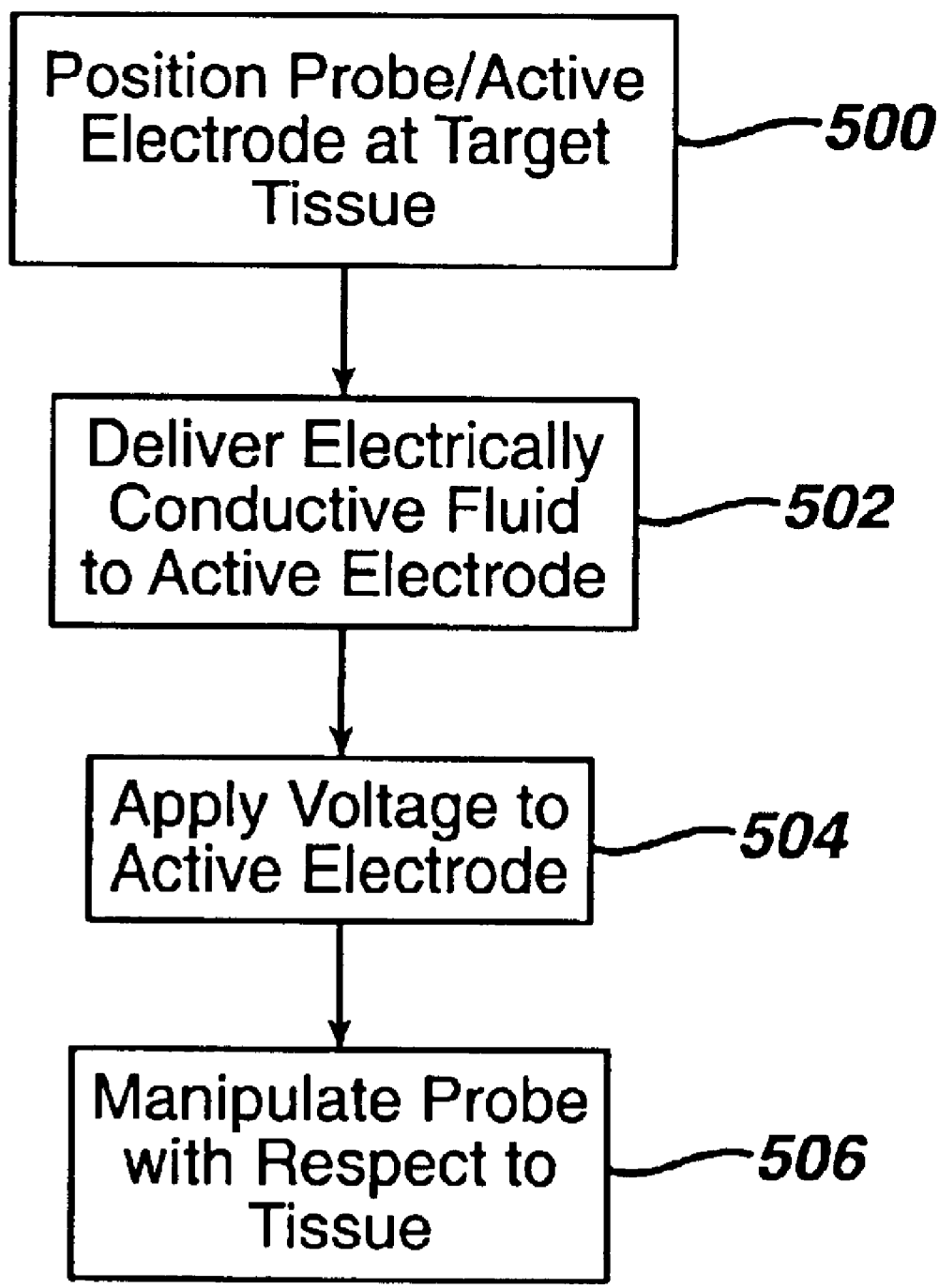

SELF-WETTING, DRY-FIELD BIPOLAR ELECTRODES FOR ENDOSCOPIC SURGERY

CROSS-REFERENCE TO RELATED APPLICATIONS

The present invention claims the benefit of earlier-filed U.S. provisional patent application Ser. No. 60/327,933, filed on Oct. 9, 2001.

FIELD OF THE INVENTION

The present invention relates to the field of bipolar electrosurgical devices for use in laparoscopic surgery, and more particularly, to the tip configuration for such a device including the arrangement of electrodes at the tip.

BACKGROUND OF THE INVENTION

Conventional electrosurgical instruments and techniques are widely used in surgical procedures because they generally reduce patient bleeding and trauma associated with cutting operations, as compared with mechanical cutting instruments and the like. Conventional electrosurgical technologies may be classified as being monopolar or bipolar. Monopolar techniques rely on external grounding of the patient, where the surgical device defines only a single electrode pole. Thus, the electric current must pass through the patient to reach the external grounding pad. Bipolar devices have two electrodes that are located in proximity to one another for the application of current between their surfaces. By being located in proximity to one another, bipolar devices have the advantage that current need not be passed through the body, but rather only between the two electrodes.

Conventional bipolar devices are commonly used to maintain or create hemostasis. Electrosurgical energy passing between the electrode poles through tissue promotes coagulation and thereby reduces bleeding. A historic limitation of these devices has been their inability to cut tissue, which greatly limits their utility.

Recently, RF bipolar generators and tools have been developed which cut tissue through the use of plasma. These systems employ a conductive fluid supply which is converted to a plasma 'bubble' on a portion of the electrode tip through the application of RF electrosurgical current. Tissue that contacts the plasma bubble experiences rapid vaporization of its cellular fluid, thereby producing a cutting effect.

Creation of a plasma 'bubble' in the conductive fluid media at the electrode tip requires a very high current density. As such, unlike conventional bipolar instruments, the electrode poles on these devices are not of generally the same size. Rather, one of the poles (active) is significantly smaller than the other (return). This configuration allows for current density sufficient to form plasma only at the active pole. When driven at reduced voltage levels that are not sufficient to form and maintain a plasma bubble, these devices can be used as conventional bipolar devices to direct current through a defined area of tissue. Thus, a single bipolar instrument is capable of both cutting and the creation/maintenance of hemostasis.

Known bipolar cutting devices employ an active electrode (s) at the distal tip of the instrument, and a return electrode in the vicinity of the distal tip, but proximal of the active electrode, as shown in FIG. 1. The active electrode is completely exposed (uninsulated) at the distal tip, and electrical energy flows from this electrode to the return electrode as indicated generally by the arrows. As the active electrode is completely exposed and unprotected, any error while placing or manipulating the device can result in unwanted damage to surrounding tissue.

It would thus be desirable to provide an improved tip design that eliminates or minimizes the potential for collateral tissue damage, thereby improving the safety and effectiveness of the device.

SUMMARY OF THE INVENTION

The devices described herein are bipolar electrosurgical devices for use in endoscopic surgery. They represent mechanical designs that are compatible with currently available vaporizing bipolar electrosurgery systems wherein a conductive media is used to provide a path for the flow of electricity between the poles of the electrodes. This technology allows such devices to be employed in a dry-field environment.

The present disclosure provides an electrosurgical probe having a distal end and a proximal end, with the distal end having a configuration defining an outer convex face and an inner concave face. At least one active electrode and at least one return electrode are mounted on the inner concave face. According to one embodiment, the outer convex face further comprises an electrically insulating material.

In another embodiment, the inner concave face further includes an outer peripheral portion, a middle peripheral portion, and an inner portion, wherein the outer peripheral portion is the active electrode, the inner portion is the return electrode, and the middle peripheral portion is an electrical insulator.

In an alternate embodiment, the at least one active electrode is positioned distal of the at least one return electrode, and in yet another embodiment, the first and second electrical insulators are further positioned on first and second lateral sides of the active electrode.

According to another embodiment, the inner concave face further includes a first side portion, a second side portion, and a middle positioned between the first and second side portions, wherein the first side portion is an active electrode, the second side portion is a return electrode, and the middle portion is an electrical insulator.

In yet another embodiment, the distal end has a length, and a width that decreases along the length in a distal direction.

An electrosurgical system is also provided including an electrosurgical probe having a distal end and a proximal end, with the distal end having a configuration defining an outer convex face and an inner concave face. At least one active electrode and at least one return electrode are mounted on the inner concave face. The electrosurgical system further includes a high frequency power supply, with the at least one active electrode being electrically coupled to a first pole of the power supply and the at least one return electrode being electrically coupled to a second pole of the power supply, and the power supply being adapted to apply high frequency voltage between the active and return electrodes.

Also provided is a method for electrosurgically treating a target tissue of a patient. The method includes the steps of providing an electrosurgical probe having a distal end having a configuration defining an outer convex face and an inner concave face, and at least one active electrode and at least one return electrode mounted on the inner concave face; positioning the active electrode in at least close proximity to the target tissue; and applying a high frequency voltage between the active and return electrodes, wherein at least a portion of the target tissue is ablated or modified.

For a further understanding of the nature and advantages of the present invention, reference should be had to the following description taken in conjunction with the accompanying drawings.

BRIEF DESCRIPTION OF THE DRAWINGS

FIGS. 4a and 4b are a side and a top view respectively of a distal end of a electrosurgical probe according to the present disclosure;

FIGS. 4c–4e are front views of the inner concave face of the distal tip of an electrosurgical probe illustrating various electrode configurations; and FIG. 5 illustrates the steps of a method for using an electrosurgical probe of the present disclosure.

DETAILED DESCRIPTION

Figure 1:
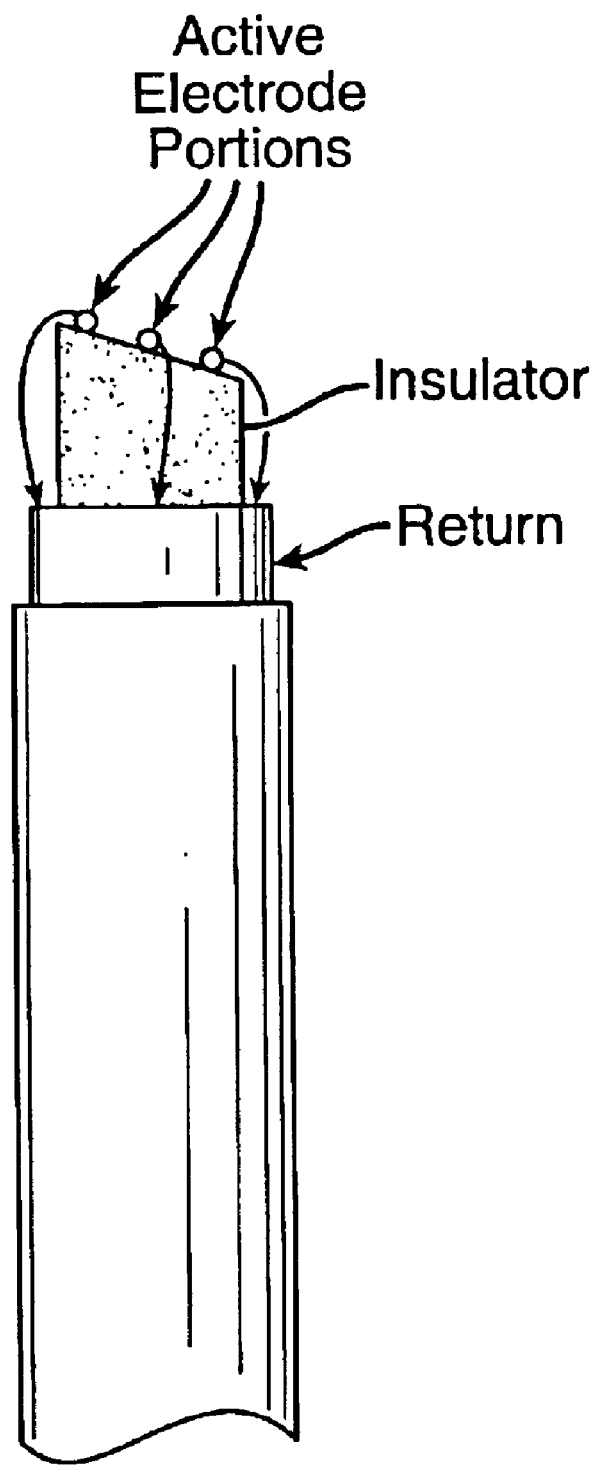
FIG. 1 illustrates a prior art tip design for an electrosurgical cutting device.
Figure 2:
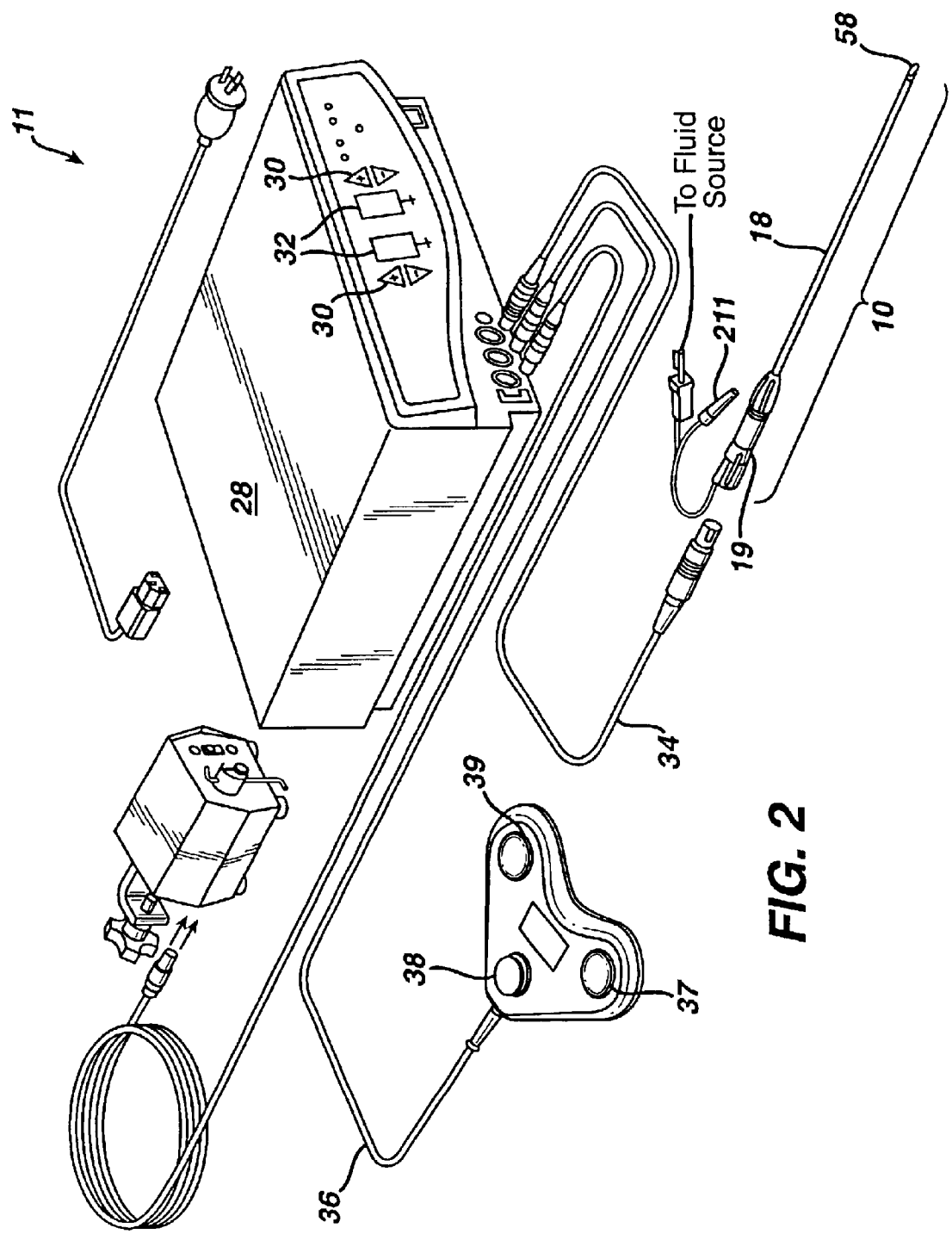
FIG. 2 is a perspective view of an electrosurgical system according to the present disclosure incorporating a power supply and an electrosurgical probe for electrosurgically treating target tissue of a patient.

Referring now to FIGS. 2–5, an exemplary electrosurgical system and method for cutting, resecting, ablating or otherwise modifying tissue will now be described in detail. As shown in FIG. 2, an exemplary electrosurgical system 11 generally comprises an electrosurgical handpiece or probe 10 connected to a power supply 28 for providing high frequency voltage, and a fluid source (not shown) for supplying electrically conductive fluid, such as saline, to the probe. In addition, the electrosurgical system may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 211 in the probe for aspirating the target site.

As shown, probe 10 generally includes a proximal handle 19 and an elongate shaft 18 having one or more active electrodes 58 at its distal end (described in more detail below). A connecting cable 34 electrically couples the active electrodes 58 to power supply 28.

Power supply 28 has operator controllable voltage level adjustments 30 to change the applied voltage level, which is observable at the voltage level displays 32. Power supply 28 also includes first, second and third foot pedals 37, 38, 39 and a cable 36, which is removably coupled to power supply 28. The foot pedals allow the surgeon to control the flow of electricity to the electrodes and remotely adjust the energy level applied to the active electrodes 58. In an exemplary embodiment, first foot pedal 37 is used to place the power supply into the "ablation" mode, second foot pedal 39 is used to place the power supply into the "coagulation" mode, and the third foot pedal 38 allows the user to adjust the voltage level within the ablation mode. In the ablation mode a sufficient voltage is supplied to the active electrodes to establish the requisite conditions for molecular dissociation of the tissue (i.e., vaporizing a portion of the electrically conductive fluid, ionizing the vapor layer, and accelerating charged particles against the tissue). The requisite level for ablation will vary depending on the number, size, shape, position and spacing of the electrodes. In the coagulation mode, the power supply 28 applies low enough voltage across the active electrodes to avoid vaporization of the electrically conductive fluid and subsequent molecular dissociation of the tissue. In this mode, electricity flowing between the active and return electrodes can be used to cause localized tissue heating and coagulation.

Figure 3:
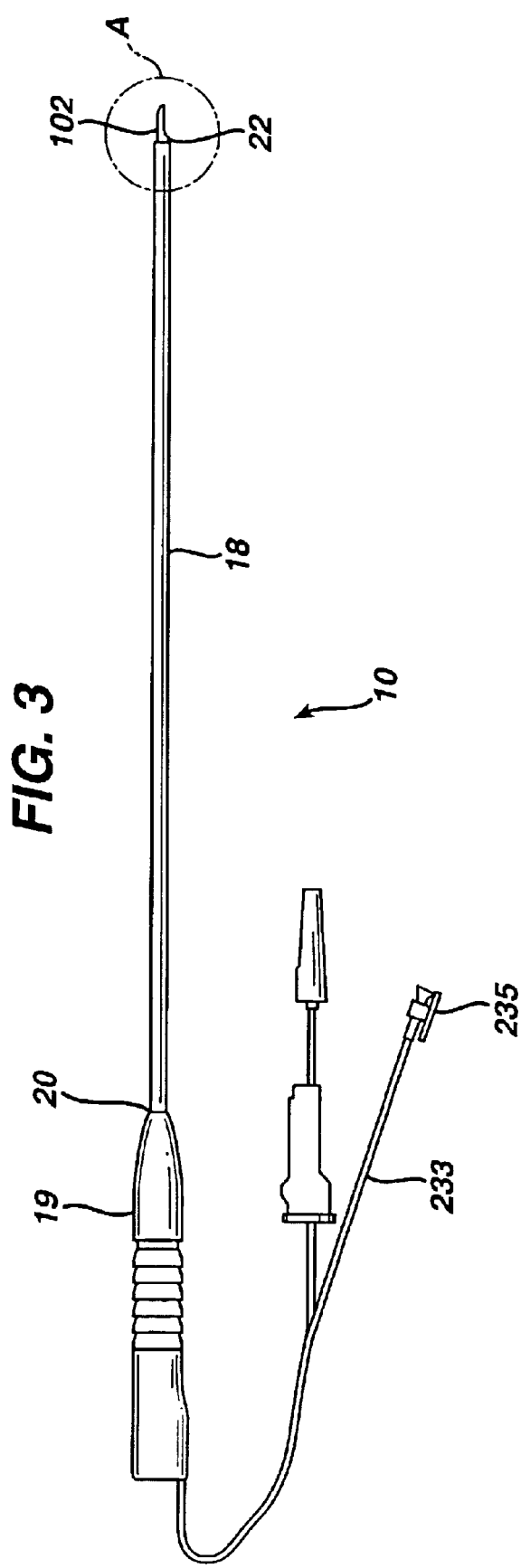
FIG. 3 is a side view of an electrosurgical probe according to the present disclosure.

FIG. 3 illustrates in greater detail an electrosurgical probe 10 that can be used in conjunction with the system of the present invention. Probe 10 generally includes an elongate shaft 18 which may be flexible or rigid, a handle 19 coupled to the proximal end 20 of the shaft and a distal end 22 of the shaft designed to support the electrodes. The distal end of the shaft and the electrode arrangements therein will be described in greater detail below. Shaft 18 may be a fiberglass composite, or comprise a plastic material that is easily molded into a desired shape, or may comprise an electrically conducting material, usually a metal such as tungsten, stainless steel alloys, platinum or its alloys, titanium or its alloys, molybdenum or its alloys, or nickel or its alloys. In the latter case, probe 10 includes an electrically insulating jacket, which is typically formed as one or more electrically insulating sheaths or coatings, such as polytetrafluoroethylene, polyimide, and the like. The provision of electrically insulated jacket over shaft 18 prevents direct electrical contact between the metal shaft and any adjacent body structure or the surgeon. Such direct electrical contact could result in unwanted heating and necrosis of the structure at the point of contact.

Handle 19 typically comprises a plastic material that is easily molded into a suitable shape for handling by the surgeons. Handle 19 defines an inner cavity (not shown) that houses an electrical connections unit that provides a suitable interface for coupling probe 10 to power supply 28 via an electrical conducting cable (i.e., 34). Electrode support member 102 extends from the distal end of shaft 18 (usually about 1 mm to 20 mm), and provides support for both active and return electrodes. A fluid tube 233 extends through an opening in handle 19, and includes a connector 235 for connection to a fluid supply source for supplying electrically conductive fluid to the target site as described above. Fluid tube 233 may be coupled to a distal fluid tube that extends through shaft 18 to an opening at the distal end of the probe. In alternate embodiments, the fluid tube may extend along the outer surface of the shaft, may be coupled to a plurality of lumina that extend through the shaft to a plurality of openings at the distal end, or may be completely independent of the shaft. Additional details regarding an electrosurgical system within which the inventive tip design described herein can be incorporated can be found in U.S. Pat. No. 5,697,281, which is incorporated herein by reference in its entirety.

The distal end of the probe will now be described in detail with reference to FIGS. 4a–4e. As shown in FIGS. 4a and 4b, the distal end 100 of the probe has a curved configuration defined by an outer convex face 102 and an inner concave face 104. Although the inner and outer faces are described as convex and concave, it is to be understood that these terms are meant to describe the overall configuration of the faces and are not to be limited to any particular geometric configuration. For example, in the illustrated embodiment, the outer convex face is defined by a substantially continuous curved surface, whereas the inner concave surface is defined by two substantially flat surfaces 104a, 104b that intersect to form the concave surface. Multiple intersecting curved and/or flat surfaces may be used to define the overall concave and convex faces described herein.

The distal end of the probe also has a length l and a varying width w. In the illustrated embodiment, the width decreases in the distal direction (tapers) so that the distal end has an overall substantially U-shaped configuration when viewed from above (FIG. 4b). According to one embodiment, the length l is approximately 1–3 cm and the width w is approximately 3–4 mm. Further dimensions of this embodiment include a tip thickness t of about 3 mm and a tip distance d of about 1–2 cm.

Referring now to FIGS. 4c–4e, the probe is a bipolar probe having at least one active electrode and at least one return electrode mounted on the inner concave face of the distal end of the probe. Mounting the electrodes on an inner concave face as described herein both reduces the potential for collateral tissue damage and facilitates manipulation of the device. The electrodes are protected or shielded from surrounding tissue by the outer convex face, thereby minimizing collateral tissue damage from active electrodes when the device is in operation, and also minimizing similar damage caused by manipulation of the device when attempting to position it in proximity to the target tissue. In one embodiment, the former benefits are even further enhanced by providing an outer convex face that is covered by or is made of an electrically insulating material such as plastic, ceramic, glass, or silicone. When plastic is employed, the high temperatures created by the vapor pocket may necessitate the inclusion of an insulating material such as silicone between the electrodes and the mounting surface.

FIGS. 4c–4e illustrate alternate embodiments for configuration of the active and return electrodes that are mounted on the inner concave face of the distal tip of the probe. For each embodiment, vaporization is intended to occur only in the vicinity of the active electrode, and to achieve this goal the return electrode must be significantly larger than the active electrode.

In the embodiment shown in FIG. 4c, the inner concave face further includes a outer peripheral portion 110 extending around and adjacent to the outer periphery 112 of the inner concave face, a middle peripheral portion 114 extending within and adjacent to the inner periphery 116 of the outer peripheral portion 110, and an inner portion 120 extending within and adjacent to the inner periphery 118 of the middle peripheral portion 114. The outer peripheral portion 110 is an active electrode (i.e., one or more active electrodes are mounted on the outer peripheral portion), the inner portion 120 is the return electrode, and the middle peripheral portion 114 is comprised of an insulating material to electrically insulate the active electrode from the return electrode. Although the active and return electrodes are referred to in the singular, it is to be understood that the active electrode may consist of multiple active electrode and the return electrode may similarly consist of multiple return electrodes.

In another embodiment illustrated in FIG. 4d, the inner concave face of the distal end of the probe includes a first side portion 130, a second side portion 132, and a middle portion 134 adjacent to the first and second side portions and separating them from one another. In this embodiment, the first side portion is the active electrode, the second side portion is the return electrode, and the middle portion electrically insulates the active and return electrodes from one another.

In yet another embodiment shown in FIG. 4e, the active and return electrodes are both mounted on the inner concave face as described above, with the active electrode being positioned distal of the return electrode. In one configuration, the return electrode 140 spans the width of the distal end of the probe, and the active electrode is mounted on an inner portion 146 of the distal tip of the probe, with electrical insulators 142, 144 positioned on first and second lateral sides of the active electrode.

FIG. 5 schematically represents typical steps involved in a method for using the electrosurgical system and probe described herein to treat a patient. Initially, the distal end of the probe is positioned relative to the target tissue so that the active electrode of the probe is in contact with, or in close proximity to, the target tissue (step 500). Next, in step 502, an electrically conductive fluid is delivered to the distal end of the probe in vicinity of the active electrode as described above. The electrically conductive fluid may be a liquid or gel, but in a preferred embodiment is isotonic saline. Following introduction of the electrically conductive fluid, the power supply 28 is activated to supply a high frequency voltage between the active and return electrodes that is sufficient to ablate or otherwise modify the target tissue via localized molecular dissection of target tissue components. The applied frequency can vary from about 30 kHz to 2.5 kHz (often from 100–200 kHz), which corresponds to about 5–1000 volts RMS (root mean square) (often 10–500 volts RMS). The actual voltage may depend on a number of factors, including the size of the active electrode, and the operating frequency.

Finally, at step 506, the active electrode is manipulated relative to the target tissue to produce the desired result at the target tissue. For example, if dissection of a particular portion of the target tissue is desired, the active electrode may be moved along a predetermined path to accomplish such dissection.

Although exemplary embodiments and methods for use have been described in detail above, those skilled in the art will understand that many variations are possible without departing from the spirit and scope of the invention, which is limited only by the appended claims.

What is claimed is:

1. An electrosurgical probe, comprising:
   a distal end and a proximal end, the distal end having a configuration defining an outer convex face having an electrically insulating material and an inner concave face; and
   at least one active electrode and at least one return electrode, the at least one active and return electrodes being located on the inner concave face wherein the inner concave face further comprises an outer peripheral portion, a middle peripheral portion, and an inner portion, wherein the outer peripheral portion is the active electrode, the inner portion is the return electrode, and the middle peripheral portion is an electrical insulator.

2. The electrosurgical probe according to claim 1, wherein the at least one active electrode is positioned distal of the at least one return electrode.

3. The electrosurgical probe according to claim 2, wherein first and second electrical insulators are positioned on first and second lateral sides of the active electrode.

4. An electrosurgical system, comprising:
   an electrosurgical probe having a distal end and a proximal end, the distal end having a configuration defining an outer convex face having an electrically insulating material and an inner concave face, and having at least one active electrode and at least one return electrode located on the inner concave face; and
   a high frequency power supply, wherein the at least one active electrode is electrically coupled to a first pole of the power supply, the at least one return electrode is electrically coupled to a second pole of the power supply, and the power supply is adapted to apply high frequency voltage between the active and return electrodes, wherein the inner concave face further comprises an outer peripheral portion, a middle peripheral portion, and an inner portion, wherein the outer peripheral portion is the active electrode, the inner portion is the return electrode, and the middle peripheral portion is an electrical insulator.

5. The electrosurgical probe according to claim 4, wherein the at least one active electrode is positioned distal of the at least one return electrode.

6. The electrosurgical probe according to claim 5, wherein first and second electrical insulators are positioned on first and second lateral sides of the active electrode.

7. A method for electrosurgically treating a target tissue of a patient, comprising:

providing an electrosurgical probe having a distal end having a configuration defining an outer convex face having an electrically insulating material and an inner concave face, and at least one active electrode and at least one return electrode located on the inner concave face, wherein the inner concave face further comprises an outer peripheral portion, a middle peripheral portion, and an inner portion, wherein the outer peripheral portion is the active electrode, the inner portion is the return electrode, and the middle peripheral portion is an electrical insulator;

positioning the active electrode in at least close proximity to the target tissue; and applying a high frequency voltage between the active and return electrodes, wherein at least a portion of the target tissue is ablated or modified.

8. The method according to claim 7, wherein the at least one active electrode is positioned distal of the at least one return electrode.

9. The method according to claim 8, wherein first and second electrical insulators are positioned on first and second lateral sides of the active electrode.

* * * * *